United States Patent
Müller

(10) Patent No.: US 6,620,429 B1
(45) Date of Patent: Sep. 16, 2003

(54) USE OF BASIC ALKALI METAL SALTS FOR MANUFACTURING TRANSDERMAL THERAPEUTIC SYSTEM

(75) Inventor: Walter Müller, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/647,688

(22) PCT Filed: Mar. 20, 1999

(86) PCT No.: PCT/EP99/01876

§ 371 (c)(1),
(2), (4) Date: Jul. 30, 2001

(87) PCT Pub. No.: WO99/49844

PCT Pub. Date: Oct. 7, 1999

(30) Foreign Application Priority Data

Mar. 30, 1998 (DE) .......................................... 198 14 083

(51) Int. Cl.⁷ .......................... A61F 13/00; A61L 16/15; A61K 9/14
(52) U.S. Cl. ........................ 424/449; 424/448; 424/443; 424/484
(58) Field of Search ................................. 424/449, 448, 424/443, 484

(56) References Cited

U.S. PATENT DOCUMENTS

| 4,781,924 A | * 11/1988 | Lee et al. .................... 424/449 |
| 4,837,027 A | 6/1989 | Lee et al. |
| 5,466,466 A | * 11/1995 | Muller ........................ 424/448 |

FOREIGN PATENT DOCUMENTS

| DE | 39 05 050 | 8/1990 |
| DE | 39 05 051 | 8/1991 |
| EP | 0 272 562 | 6/1988 |
| EP | 0 593 807 A | 4/1994 |

* cited by examiner

Primary Examiner—Thurman K. Page
Assistant Examiner—Isis Ghali
(74) Attorney, Agent, or Firm—D. Peter Hochberg; Katherine R. Vieyra; Sean Mellino

(57) ABSTRACT

A process for manufacturing transdermal systems comprising free active substance bases is characterized in that the free active substance base is liberated, during the manufacture of the system, from active substance salts by conversion with a basic alkaline metal salt.

12 Claims, No Drawings

USE OF BASIC ALKALI METAL SALTS FOR MANUFACTURING TRANSDERMAL THERAPEUTIC SYSTEM

BACKGROUND OF THE INVENTION

1. Field of the Invention

Many medicinal active agents contain one or more basic nitrogen atoms in their molecule and can therefore be utilized in pharmaceutical preparations either as a free base or as a salt of the active substance base with an acid which is suitable for this purpose. Salts have the advantage of better water solubility, which is important for oral administration, and in many cases also the advantage of better stability. A further advantage is that active substance salts are often more easily crystallised, or it is anyway only the active substance salt which is crystalline at room temperature. This is the reason why many active substances are manufactured and available only in the form of their salts.

2. Description of the Preferred Embodiment

For transdermal administration, however, the active substance salts are unsuitable since due to their higher polarity they are not capable of penetrating the lipophile barrier of the stratum corneum in the quantities required for the therapeutic purpose.

Thus, it is necessary to transform active substance salts into their free base in order to utilize them in transdermal systems.

Basically, there are two types of transdermal therapeutic systems (TTSs) which dominate the market, namely the so-called matrix systems and the reservoir systems.

A matrix system consists in the simplest case of a backing layer, a self-adhesive active agent-containing matrix, and a protective film or sheet which is to be removed prior to use. In more complicated designs, the matrix has a multi-layer structure, while there is no necessity for each of the layers to be self-adhesive. Incorporation of membranes into the matrix for control of active substance delivery may also be provided.

A matrix system may also consist of a non-self-adhesive active substance-containing matrix which, for fixation on the skin, is provided with an active substance-free superimposed patch which projects beyond said matrix on all sides.

Reservoir systems consist of a bag made of an active substance-impermeable film or sheet, and a membrane which is permeable at least to the active substance. The bag is filled with a liquid or gel-like active substance preparation. For anchoring the system on the skin, the membrane is in most cases equipped with an adhesive. These systems, too, are provided with a protective sheet to be removed prior to use.

Technically, it is of course no problem to convert an active substance salt into the free base. The most simple way to achieve this is to dissolve the active substance salt in water and to add an auxiliary base such as NaOH. The resultant active substance base either precipitates on account of its lesser water-solubility and can be filtered off, or it must be extracted with a suitable organic solvent, such as methylene chloride. A disadvantage of this procedure is that the free base must be specially processed so as to be usable for the manufacture of the transdermal systems.

An ideal process enables the release of the free base during the manufacture of the system in situ without the manufacturing process thereby becoming considerably more complicated than in the case of direct use of the free base.

Such a process is described in EP 0 272 562. In this process, adhesives are used which themselves possess basic groups and are thereby themselves, as auxiliary bases, capable of liberating the free base. The disadvantage of this process is that the number of these functional basic groups in the adhesive is limited, and that for this reason only small amounts of active substance salts can be converted into their free bases.

SUMMARY OF THE INVENTION

It is the object of the present invention to develop a process which enables the conversion also of larger amounts of active substance and accordingly avoids the disadvantages of the prior art.

DESCRIPTION OF THE PREFERRED EMBODIMENTS

Surprisingly, it was found that it is possible to convert active substance salts in organic solvents, such as methanol, ethanol, ispropanol, methyl ethyl ketone, into their free bases by conversion with basic alkaline metal salts, especially alkaline silicates, such as trisilicates and metasilicates of sodium or potassium. Trisilicates and metasilicates are available in various degrees of hydration, which are, however, to be regarded as equivalent in terms of their suitability.

These silicates are salts of a weak acid with a strong base, and therefore react as a base. This means that in the presence of active substance salts which are to be considered weak acids they are converted to the free silicic acids. The free silicic acids are unstable and react further to polymeric silicon dioxide under elimination of water. This makes the reaction irreversible, and the complete conversion of the active substance salts into their free bases is possible despite the low basicity of the silicates. A precondition thereof is of course that the silicate is used at least in the stoichiometrically required amount. The fact that the reaction is irreversible renders the silicates superior to other auxiliary bases such as ethanolamines, since the latter compounds possess a basicity comparable to that of the active substance bases, with the result that only equilibriums occur wherein an almost quantitative conversion of the active substance salt into the free base is possible only under use of an excess of auxiliary base. In addition, these auxiliary bases are themselves capable of entering the skin or permeating therethrough and of causing local skin irritations or toxic side effects.

It is surprising and unexpected that alkaline metal silicates, especially trisilicates and metasilicates of sodium and potassium, can be utilized for this purpose in organic solvents since both the active substance salts and the silicates have only very low solubility in these solvents.

The best solubility for these silicates was found in methanol and ethanol and was determined to be only 0.01% (g/g). Nevertheless, it is possible to use solvents with even less solubility for silicates, such as isopropanol, acetone, methyl ethyl ketone, ethyl acetate and mixtures of the aforementioned solvents.

It is furthermore surprising that despite this low solubility one is successful in achieving, within acceptable periods of time, a complete conversion of the active substance salts into their free bases. Normally, the complete conversion at room temperature takes only about 2–3 days; it can be shortened to about 24 hours by increasing the temperature to about 35–40° C. Attempts to use silicates of calcium or magnesium failed since, owing to the multivalent cations, they are practically insoluble in organic solvents. Basic aluminium-containing mixed silicates have proved just as unsuitable.

it is possible to check microscopically if the conversion has been completed. If the conversion is complete, none of the active substance salt crystals, which are poorly soluble in organic solvents, are visible any more.

For the manufacture of matrix systems it is important that the solvents used for the conversion are highly compatible with the adhesives dissolved in organic solvents. This is the case with the above-mentioned solvents, however, the selection mentioned is only exemplary.

Reaction products of the alkaline silicates are silicon dioxide and the sodium or potassium salt of the acid contained in the active substance. Silicon dioxide is a compound which is to be considered totally atoxic. For this reason, from the toxicological standpoint, it is not necessary to remove silicon dioxide from the active substance solution. Should this be required from a technical point of view, one only needs to include a filtration step.

Also, the basic silicates themselves are to be regarded as practically atoxic. They are utilized without problems in many industrial or household detergents to set the detergent to a basic pH. The only reaction which might possibly have to be expected is skin irritation due to their basicity. Since, however, their solubility in the polymers or reservoir formulations used for matrix systems is low, this too is normally not to be expected. Only in the case of very high concentrations, which in matrix systems lead to the undissolved silicate crystals coming into contact with the skin, there is a risk of local skin irritations. However, by filtering-off one can very easily remove any excess silicates in the converted active substance solution. The filtration step is also advisable if the active substance tends to show instabilities in the presence of basic substances. After filtration, the pH in the TTS matrix, or in the reservoir of the reservoir systems, is determined only by the basicity of the active substance itself—if no other pH regulators are added.

The use of basic alkaline metal salts, in particular, of alkaline metal silicates, and especially of metasilicates and trisilicates of sodium or potassium, for in-situ conversion of salts of basic active substances into the free active substance bases during the manufacture of transdermal therapeutic systems, represents a considerable improvement over the prior art. The conversion takes place under very mild conditions, and it is not necessary to isolate the active substance base or to separate the reaction products of the auxiliary base. Possible unreacted excess amounts of the silicates need not be separated either, since as a consequence of their being incorporated in the transdermal system there is no risk of any side effects whatsoever.

EXAMPLES

Example 1

20 g of (−)-5,6,7,8-tetrahydro-6-[propyl[2-(2-thienyl)-ethyl]amino]-1-naphthol hydrochloride are stirred, together with 8.0 g of sodium metasilicate or 9.1 g of sodium trisilicate, in 35 ml of ethanol for 48 hours at room temperature. Optionally, the active substance solution is now filtrated, and 6.0 g of polyvinyl pyrrolidone (Kollidon F90, from Bayer), in the form of a 25% (g/g) solution in ethanol, and 250 g of a 70% solution of an amino-resistant silicone adhesive (Q7-4301, from Dow Corning) in heptane are added, and the mass is subsequently homogenised by mechanical stirring.

Subsequently, in order to prepare the patch matrix the mass is coated on an appropriate, abhesively equipped film, and the solvents are removed by drying for 20 minutes at 50° C. The coating weight of the dried matrix film is 50 g/m$^2$.

The dried matrix film is laminated with a 23-$\mu$m-thick polyester film. The individual plasters are punched out of the complete laminate.

Example 2

25 g of (−)-5,6,7,8-tetrahydro-6-[propyl[2-(2-thienyl)ethyl]amino]-1-naphthol hydrochloride are stirred, together with 14.7 g of sodium metasilicate or 16.8 g of sodium trisilicate, in 40 ml of ethanol for 48 hours at room temperature. Optionally, the active substance solution is now filtrated, and 9.2 g of oleyl alcohol, 63.2 g of a 52% solution of a polyacrylate adhesive (Durotak 387–2287, from National Starch & Chemical), and 22.8 g of a 4004 (g/g) solution of Eudragit E 100 (Röhm-Pharma) are added, and the mass is subsequently homogenised by mechanical stirring.

Subsequently, for preparation of the patch matrix, the mass is coated on an appropriate, abhesively equipped film, and the solvents are removed by drying for 20 minutes at 50° C. The coating weight of the dried matrix film is 80 g/m$^2$.

The dried matrix film is laminated with a 23-$\mu$m-thick polyester film. The individual plasters are punched out of the complete laminate.

Example 3

50 g of scopolamine hydrobromide are stirred, together with 13.8 g of sodium metasilicate or 15.7 g of sodium trisilicate, in 40 ml of ethanol for 48 hours at room temperature. Optionally, the active substance solution is now filtrated, and 32 g of oleic acid and 480 g of a 52% solution of a polyacrylate adhesive (Durotak 387–2253, of National Starch & Chemical) are added, and the mass is subsequently homogenised by mechanical stirring.

Subsequently, for preparation of the patch matrix, the mass is coated on an appropriate, abhesively equipped film, and the solvents are removed by drying for 20 minutes at 50° C. The coating weight of the dried matrix film is 90 g/m$^2$.

The dried matrix film is laminated with a 23-$\mu$m-thick polyester film. The individual plasters are punched out of the complete laminate.

The invention has been described with particular emphasis on the preferred embodiments, but variations and modifications within the spirit and scope of the invention may occur to those skilled in the art to which the invention pertains.

What is claimed is:

1. A process for manufacturing transdermal systems comprising free active substance bases, said process comprising the steps of manufacturing the systems and liberating the free active substance base by converting active substance salts with a basic alkaline metal salt, wherein said basic alkaline metal salt is a silicate, and wherein the active substance salts are converted in an organic solvent.

2. The process for manufacturing transdermal systems comprising free active substance bases according to claim 1, wherein the silicate is selected from the group consisting of a sodium and potassium silicate.

3. The process for manufacturing transdermal systems comprising free active substance bases according to claim 1 wherein the silicate is selected from the group consisting of a trisilicate and metasilicate.

4. The process for manufacturing transdermal systems comprising free active substance bases according to claim 1, wherein the organic solvent is selected from the group consisting of ethanol, methanol, methyl ethyl ketone, isopropanol, ethylene glycol, propylene glycol and mixtures thereof.

5. The process for manufacturing transdermal systems according to claim 1, comprising the additional steps of suspending the active substance salt along with the basic alkaline metal salt in the organic solvent to form a solution or suspension, stirring the solution until quantitative conversion of the active substance salt is achieved, and[, subsequently] adding the quantitative converted active substance salt to a polymer mass which is dissolved in an organic solvent.

6. The process for manufacturing transdermal systems cording to claim 5, wherein the dissolved polymer mass is an adhesive.

7. The process for manufacturing transdermal systems according to claim 5 comprising the additional step of filtering the solution or suspension of the basic alkaline metal salt and the active substance salt following the conversion and prior tobing added to the polymer mass.

8. The process for manufacturing transdermal systems according to claim 6 wherein for manufacture of a matrix system, comprising the additional steps of coating the polymer mass on a suitable, adhesively equipped film or sheet, drying the film or sheet to remove the solvents, laminating the dried film with a suitable film or sheet, and punching out the transdermal systems from the resultant laminate.

9. The process for manufacturing transdermal systems according to claim 6 for manufacture of a reservoir system, and further comprising the steps of completely converting the active substance salt, and filling a bag comprising an impermeable backing layer and a membrane permeable at least to the active substance with the solvent.

10. The process for manufacturing transdermal systems according to claim 9, and further comprising the steps of providing the membrane of the bag with an adhesive layer for adhesion to the skin.

11. The process for manufacturing transdermal systems according to claim 1, wherein the active substance is selected from the group consisting of antihypersensitives, antiemetics, antiparkinsonian agents, antidepressants, antiasthmatics, analgesics and antiallergic agents.

12. The process for manufacturing transdermal systems according to claim 1, wherein that the active substance is a D2-agonist and especially (−)-5,6,7,8-tetrahydro-6-[propyl [2-(2-thienyl)ethyl]amino]-1-naphthol.

* * * * *